(12) United States Patent
Kim et al.

(10) Patent No.: US 9,207,063 B2
(45) Date of Patent: Dec. 8, 2015

(54) OPTICAL COHERENCE TOMOGRAPHY USING ACTIVE MODE-LOCKING FIBER LASER

(75) Inventors: Chang Seok Kim, Busan (KR); Myung Yung Jeong, Busan (KR); Hwi Don Lee, Seoul (KR)

(73) Assignee: PUSAN NATIONAL UNIVERSITY INDUSTRY-UNIVERSITY COOPERATION FOUNDATION, Pusan (KR)

(*) Notice: Subject to any disclaimer, the term of this patent is extended or adjusted under 35 U.S.C. 154(b) by 0 days.

(21) Appl. No.: 13/814,061
(22) PCT Filed: Jul. 28, 2011
(86) PCT No.: PCT/KR2011/005571
§ 371 (c)(1), (2), (4) Date: Feb. 21, 2013
(87) PCT Pub. No.: WO2012/018195
PCT Pub. Date: Feb. 9, 2012

(65) Prior Publication Data
US 2013/0169972 A1 Jul. 4, 2013

(30) Foreign Application Priority Data
Aug. 4, 2010 (KR) .................. 10-2010-0075260

(51) Int. Cl.
*G01B 9/02* (2006.01)
*G01N 21/47* (2006.01)
(Continued)

(52) U.S. Cl.
CPC ........ *G01B 9/02091* (2013.01); *G01B 9/02004* (2013.01); *G01N 21/31* (2013.01); *G01N 21/4795* (2013.01); *H01S 3/067* (2013.01);
(Continued)

(58) Field of Classification Search
CPC .......... G01B 9/02091; G01B 9/02001; G01B 9/02002; G01B 9/0201; G01N 21/4795; G01N 21/31
USPC .................................... 356/479, 497
See application file for complete search history.

(56) References Cited

U.S. PATENT DOCUMENTS 8,315,282 B2 * 11/2012 Huber et al. .................. 372/18
2007/0091941 A1 * 4/2007 Mori et al. ................... 372/18
(Continued)

FOREIGN PATENT DOCUMENTS

| JP | 2002-335039 A | 11/2002 | |
|---|---|---|---|
| JP | 2005-093498 A | 4/2005 | |
| JP | 2009-031238 A | 2/2009 | |
| JP | WO 2009/139481 | * 11/2009 | ............. H01S 3/067 |
| KR | 10-2000-0066752 A | 11/2000 | |

OTHER PUBLICATIONS

International Search Report for PCT/KR2011/005571 mailed Mar. 21, 2012 from Korean Intellectual Property Office.

*Primary Examiner* — Jonathan Hansen
(74) *Attorney, Agent, or Firm* — Paratus Law Group, PLLC

(57) ABSTRACT

Discloses is an optical coherence tomography (OCT) which uses an active mode-locking fiber laser in order to obtain image information of a sample. An imaging device in accordance with an embodiment comprises: a light source unit; a light separation unit; a reference unit; a diagnostic unit; a light coupling unit; and a signal processing unit. The imaging device removes a high-priced variable filter which has mechanical restrictions by directly delivering a modulation signal to a light source unit, so it can overcome mechanical restrictions and reduce costs.

7 Claims, 5 Drawing Sheets

(51) Int. Cl.
*H01S 3/067* (2006.01)
*H01S 3/11* (2006.01)
*G01N 21/31* (2006.01)
*H01S 3/23* (2006.01)

(52) U.S. Cl.
CPC ........... *H01S 3/1112* (2013.01); *H01S 3/06791* (2013.01); *H01S 3/2383* (2013.01)

(56) References Cited

U.S. PATENT DOCUMENTS

2010/0097614 A1    4/2010  Kourogi et al.
2011/0155916 A1*   6/2011  Furusawa et al. ........ 250/363.04
2013/0329757 A1*  12/2013  Huber et al. .................... 372/18

* cited by examiner

OPTICAL COHERENCE TOMOGRAPHY USING ACTIVE MODE-LOCKING FIBER LASER

CROSS REFERENCE TO PRIOR APPLICATION

This application is a National Stage Patent Application of PCT International Patent Application No. PCT/KR2011/005571 (filed on Jul. 28, 2011) under 35 U.S.C. §371, which claims priority to Korean Patent Application No. 10-2010-0075260 (filed on Aug. 4, 2010), which are all hereby incorporated by reference in their entirety.

BACKGROUND OF THE INVENTION

1. Field of the Invention

The present invention relates to an optical coherence tomography, and more particularly, an optical coherence tomography using an active mode-locking fiber laser having a center wavelength which is changed by a high speed repeated scanning.

2. Description of the Related Art

A detecting system using a light space division comprises an optical coherence tomography (OCT) obtaining an image-in-depth of a sample with the coherence of light. The optical coherence tomography is a high-resolution imaging system capable of imaging of internal tissue of a sample. The optical coherence tomography uses interference of a light source in near infrared ray wavelength. Particularly, the optical coherence tomography does not contact the inside of a sample for imaging, and recently, the related studies have been actively conducting.

In the optical coherence tomography, an acquisition rate of information in depth direction is dependent on a repetition rate of a center wavelength variable laser. Unlikely, the scanning along a horizontal axis and a vertical axis should be done when obtaining two-dimensional or three-dimensional image from the optical coherence tomography.

Thus, conventional optical coherence tomography requires an optical variable filter to periodically scan laser wavelength and convert wavelength. Fabry-perot filter is mainly used for this optical variable filter.

Meanwhile, there is a problem of degradation characteristics of the optical variable filter with mechanical restrictions in the frequency domain over hundreds of kHz. Also, these optical variable filters are relatively expensive, and cost of producing optical coherence tomography increases.

SUMMARY OF THE INVENTION

Accordingly, the present invention is conceived to solve the aforementioned problems in the prior art. An objection of the present invention is to provide an active mode-locking fiber laser, wherein a center wavelength of laser is selected by an optical amplifier of a light source unit or frequency of a RF modulation signal repeating the rapid rise and fall of the light intensity of an electro optical device, not by a center wavelength of a high-priced optical variable filter.

Another object of the present invention is to provide an optical coherence tomography, wherein periodically repeated changes of the laser center wavelength are provided by periodically changing frequency of a modulation signal, not by periodically changing a center wavelength of a conventional optical variable filter, thereby overcoming mechanical restrictions and reducing costs.

An optical coherence tomography using an active mode-locking fiber laser in accordance with the embodiments of the present invention comprises: a light source unit that emits light having a center wavelength which is periodically changed by a modulation signal received from the inside of a resonator; a light separation unit that separates the light having a single path, which is emitted from the light source unit, into a first light and a second light having different paths; a reference unit that is disposed on a path through which a first light separated by the light separation unit progresses, and reflects the first light; a diagnostic unit that has a sample mounted thereon, is disposed on a path of a second light separated by the light separation unit, and the second light is delayed more than the first light for a certain time to reflect the delayed light; a light coupling unit that couples a first light and a second light, which are progressed in different paths through the reference unit and the diagnostic unit and in which mutual interference is generated therefrom; and a signal processing unit that detects and images data of the light received from the light coupling unit.

In the embodiments of the present invention, the light source comprises an optical amplifier providing optical gains to a ring shaped resonator and receiving the modulation signal, a dispersive compensation fiber compensating the optical dispersion in the resonator, and an output coupler continuously waving light reflection and transmission in the resonator at certain rates.

In other embodiments of the present invention, the light source comprises an optical amplifier providing optical gains to a linear resonator with mirrors at both ends, and receiving the modulation signal; a dispersive compensation fiber compensating the optical dispersion in the resonator; and an output coupler continuously waving light reflection and transmission in the resonator at certain rates.

In other embodiments of the present invention, the light source comprises an optical amplifier providing optical gains to a ring shaped resonator; an electro optical device switching the progress of light depending on the intensity of light received from the optical amplifier, and receiving the modulation signal; a dispersive compensation fiber compensating the optical dispersion in the resonator; and an output coupler continuously waving light reflection and transmission in the resonator at certain rates.

In other embodiments of the present invention, the light source unit comprises an optical amplifier providing optical gains to a linear resonator with mirrors at both ends; an electro optical device switching the progress of light depending on the intensity of light received from the optical amplifier, and receiving the modulation signal; a dispersive compensation fiber compensating the optical dispersion in the resonator; and an output coupler continuously waving light reflection and transmission in the resonator at certain rates.

In other embodiments of the present invention, the light source unit comprises a plurality of optical amplifiers providing optical gains to ring shaped resonators, wherein a plurality of resonators are connected in parallel; a coupler coupling lights each emitted by the plurality of optical amplifiers; an electro optical device switching the progress of light depending on the intensity of light coupled by the coupler, and receiving the modulation signal; a dispersive compensation fiber compensating the optical dispersion passed through the electro optical device; and an output coupler continuously waving light reflection and transmission of light that passed through the dispersive compensation fiber at certain rates.

In other embodiments of the present invention, the light source unit comprises a plurality of optical amplifiers each disposed in linear resonators, wherein a plurality of resonators are connected in parallel with mirrors at both ends and a plurality of mirrors at one end, providing optical gains; a coupler coupling lights each emitted by the plurality of optical amplifiers; an electro optical device switching the progress of light depending on the intensity of light coupled by the coupler, and receiving the modulation signal; a dispersive compensation fiber for compensating the optical dispersion of the resonator; and an output coupler continuously waving optical reflection and transmission of the resonator at certain rates.

For example, the optical amplifiers can provide different optical gains in the plurality of resonators connected in parallel.

In the embodiments of the present invention, the device can further comprise a modulation signal generator for delivering a modulation signal having a changeable center frequency to the optical amplifier or the electro optical device. At this point, the modulation signal generator comprises a function generator generating certain waveform signals, and periodically changing the center frequency of the generated signals; an RF signal generator generating signal having a changeable center frequency into a certain range of RF signal; a DC voltage supply supplying a certain size DC voltage in order to control offset voltage; and a bias-tee providing the modulation signal by combining the DC voltage and the RF signal.

From the aforementioned optical coherence tomography using an active mode-locking fiber laser of the present invention, the following effects can be expected.

First, since a modulation signal having a changeable center frequency is directly inputted into a light source unit, a variable filter having mechanical restrictions can be removed.

Second, production costs for an optical coherence tomography can be reduced by replacing a high-priced variable filter with a lower-priced modulation signal generator.

Third, since a modulation signal generator is irrelevant to the length of a resonator, a light source unit, a wavelength variable speed can be changed.

Fourth, it can be stably driven with a relatively lower power by repeating the rise and fall of the light intensity by switching passive optical waveguide, without switching positive optical gains by inputting a modulation signal into an electro optical device of a light source unit.

Fifth, a plurality of light source units, laser resonators, are connected in parallel, and a modulation signal is inputted into an electro optical device disposed on a common optical path, thereby expanding the broadband and greatly improving the output efficiency.

DESCRIPTION OF THE PREFERRED EMBODIMENT

Hereinafter, preferred embodiments of an optical coherence tomography using an active mode-locking fiber laser according to the present invention will be described in detail with reference to the accompanying drawing. Since various modifications and changes can be made, the present invention will be clarified hereinafter through detailed descriptions on the embodiments. However, it is not for a limitation on the invention, therefore it is necessary to understand that all differences, equivalents, and substitutes within the equivalence to the scope will be considered to fall in the scope of the present invention. With describing each drawing, similar reference marks are provided on similar elements. In the accompanying drawing, structures are enlarged in size for the sake of clarity of the invention, or reduced in size for achieving a understanding of outlined configuration.

Also, terms like 1 and 2 can be used to describe various elements, but the elements should not be limited by the terms. The terms are used only for differentiate one element from other elements. For example, 1 element can be named 2 element within the scope of the present invention, similarly 2 element can be named 1 element. Unless defined otherwise, all technical and scientific terms used herein have the same meaning as commonly understood by one of ordinary skill in the art. Commonly used terms, which is in the dictionary, need to be read as textual meaning of the related technique. Unless defined clearly, they should not be interpreted as ideal or excessively formal meanings.

Figure 1:
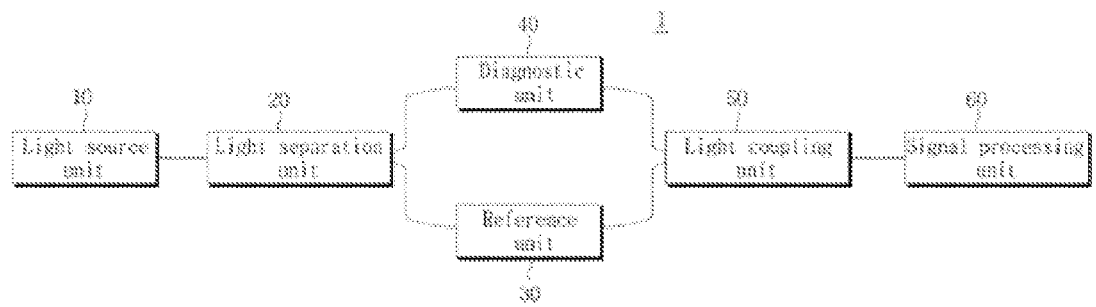
FIG. 1 is a rough block diagram illustrating an optical coherence tomography using an active mode-locking fiber laser according to the embodiments of the present invention.

FIG. 1 is a rough block diagram illustrating an optical coherence tomography using an active mode-locking fiber laser according to the embodiments of the present invention. Referring to FIG. 1, an optical coherence tomography (1) using an active mode-locking fiber laser according to the embodiments of the present invention obtains image information of a sample using interference of a light. To achieve this, an optical coherence tomography (1) comprises a light source unit (10), a light separation unit (20), a reference unit (30), a diagnostic unit (40), a light coupling unit (50), a signal processing unit (60).

A light source unit (10) emits light using a resonator. At this point, light emitted by a light source unit (10) has a single path. Also, a light source unit (10) emits light having a center wavelength which is periodically changed.

In the embodiments of the present invention, a light source unit (10) emits light having a center wavelength which is periodically changed by a modulation signal received from outside to inside of a resonator. For example, the modulation signal is a RF modulation signal. That is, a light source unit (10) directly receives a modulation signal, in which a wavelength is periodically changed, from outside, without using a variable filter periodically scanning and varying the wavelength of light that is disposed in a resonator.

On this, a light source unit (10) can emit light having a center wavelength which is periodically changed without mechanical restrictions, regardless of the length of a resonator. Also, a light source unit (10) does not relate to the length of a resonator, and there can be wide variation of wavelength variable speed. Furthermore, a light source unit can select a center wavelength of the emitted laser, with a RF modulation signal repeating the rapid rise and fall of the light intensity of an optical amplifier or an electro optical device disposed on a light source unit.

Meanwhile, the modulation signal controls the light intensity of an optical amplifier or an electro optical device, and changes the optical phase propagated inside the resonator. A optical source unit can emit laser light outside, as optical phase is changed by the modulation signal.

The above will be described in detail with reference FIGS. 2-8.

A light separation unit (20) separates light from a light source unit (10). A light separation unit (20) separates light having a single path, which is emitted from the light source unit (10), into a dispersed light having a plurality of paths. At this point, a dispersed light is one in which there exists a plurality of lights progressed into each path. For example, a light separation unit (20) comprises a 1*N coupler breaking a single input value into multiple output values. Accordingly, a light separation unit (20) separates light from a light source unit (10) into a plurality of lights. At this point, a light separation unit (20) separates light having a single path, which is emitted from a light source unit (10), into a first light and a second light having different paths.

A reference unit (30) is disposed on a path through which a first light separated by the light separation unit (20) progresses, and reflects the first light. For example, a reference unit (30) comprises a mirror (not shown), and reflects the inputted light directly. Unlikely, a reference unit (30) can delay the time from the mirror reflection, using a delay element delaying the progressing of light without reflection.

A diagnostic unit (40) that has a sample mounted thereon, is disposed on a path of a second light separated by a light separation unit (20), and the second light is delayed more than the first light for a certain time to reflect the delayed light. At this point, a second light through a diagnostic unit (40) is delayed more than a first light since a first light is reflected through a mirror in a reference unit (30), but a second light is incident on a sample and then reflects. In this process, interference of a first light and a second light may occur.

The interference of a first light and a second light, which pass through a reference unit (30) and a diagnostic unit (40), is occurred due to a path difference, and the interfering signal is produced.

A light coupling unit (50) proceeds progressing in a single path by coupling a first light and a second light, which are progressed in different paths through a reference unit (30) and a diagnostic unit (40) and in which mutual interference is generated therefrom. At this point, a light coupling unit (50) is equipped with a coupler, not coupling light itself of a first light and a second light, and proceeds light progressing in a single path.

A signal processing unit (60) detects and images data of the light received from a light coupling unit (50). A signal processing unit (60) can obtain the information about a sample with phase shift of the inputted light.

Figure 2:
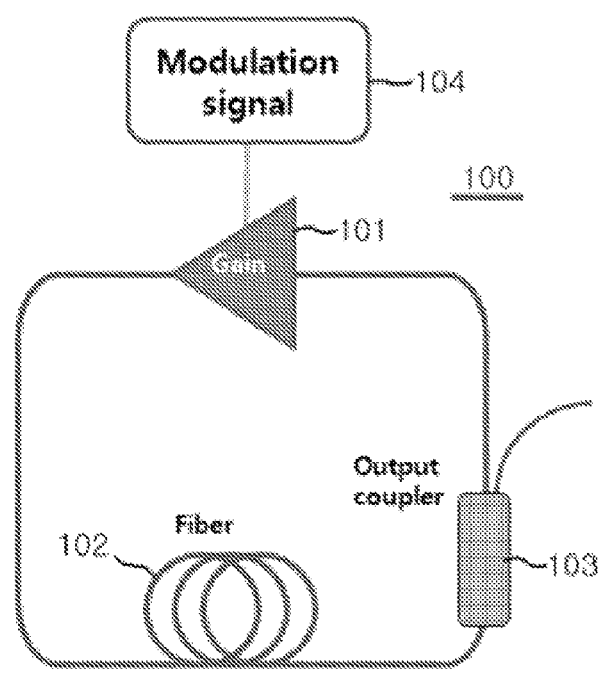
FIG. 2 is a block diagram illustrating one embodiment of a light source unit shown in FIG. 1.

FIG. 2 is a block diagram illustrating one embodiment of a light source unit shown in FIG. 1.

Referring to FIG. 2, a light source unit (100) directly receives a modulation signal having a changeable center wavelength from outside, and emits the light outside through components of a resonator.

To achieve this, a light source unit (100) comprises an optical amplifier (101) providing optical gains to a ring shaped resonator, and receiving the modulation signal; a dispersive compensation fiber (DCF) (102) compensating the optical dispersion of the resonator; and an output coupler (103) continuously waving optical reflection and transmission of the resonator at certain rates.

An optical amplifier (101) comprise a semiconductor optical amplifier or an erbium-doped fiber amplifier. The semiconductor optical amplifier and the erbium-doped fiber amplifier have already opened to the public, and so a detailed description thereof will be omitted. Those can be properly selected and used by one of ordinary skill in the art.

An optical amplifier (101) receives a certain amount of power by a power supply (not shown), and the amount of power supplied to an optical amplifier (101) is determined associated with the internal loss rate of a resonator. That is, an optical amplifier (101), which is operated by the power supplied from the power supply, acts as a gain medium, and thus it can regulate the power supply for sufficient observation of the light intensity in an output coupler (103).

Meanwhile, since a supplying power level of the power supply determines a laser light intensity of an optical amplifier (101), it is necessary to properly determine the power of the power supply for certain gains. That is, a valid laser pulse train can be obtained only if the gain of an optical amplifier (101) is higher than the internal loss of a resonator.

In the embodiments of the present invention, an optical amplifier (101) of an light source unit (100) directly receives a modulation signal from a modulation signal generator (104). At this point, a modulation signal generator (104) can be equipped with a separate light source unit (100), and can be disposed in a light source unit (100).

A light source unit (100), to modulate a center wavelength of a laser light, directly receives a modulation signal having a changeable center wavelength from a modulation signal generator (104), not using a variable filter, and there can be wide variation of wavelength variable speed, regardless of the length of a resonator. Also, the cost of producing the tomography (1) with a light source unit (100) can be significantly reduced by removing a high-priced variable filter having mechanical restrictions. Furthermore, a light source unit (100) can select a center wavelength of the emitted laser light, with a RF modulation signal repeating the rapid rise and fall of the light intensity of an optical amplifier (101) or an electro optical device disposed on a light source unit (100).

Figure 3:
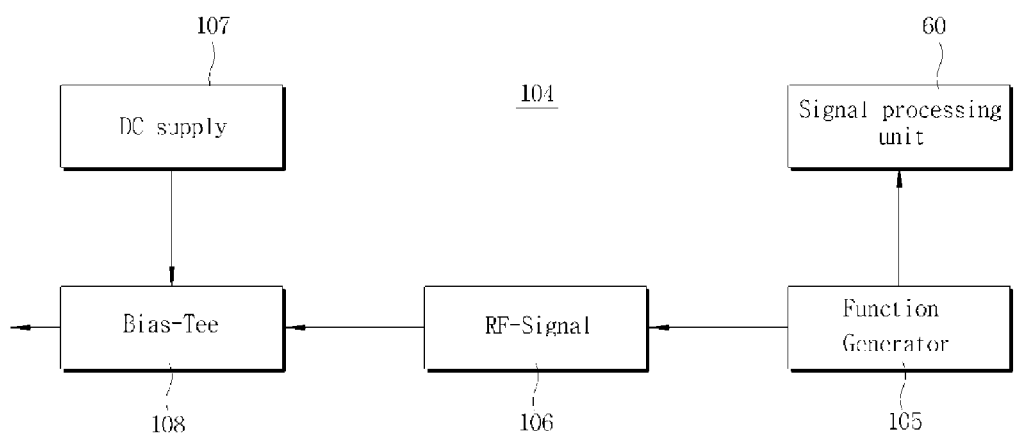
FIG. 3 is a block diagram concretely illustrating a modulation signal generator shown in FIG. 2.

FIG. 3 is a block diagram concretely illustrating a modulation signal generator shown in FIG. 2.

Referring to FIG. 3, an imaging device according to the embodiments of the present invention further comprises a modulation signal generator (104) providing a modulation signal to a light source unit (100). A modulation signal generator (104) delivers a modulation signal having a changeable center wavelength to an optical amplifier (101) of a light source unit (100).

In the embodiments of the present invention, a modulation signal generator (104) comprise a function generator (105), a RF signal generator (106), a DC supply (107) and a bias-tee (108).

A function generator (105) generates signals such as a triangular waveform or a ramp waveform. Also, a function generator (105) periodically change and deliver the center wavelength of the generated signal. For example, a function generator (105) generates a signal with frequency of 100 kHz.

Meanwhile, a function generator (105) generates signals such as a triangular waveform or a ramp waveform at a lower repetition rate, and generates signals such as a sinusoidal waveform at a high repetition rate. Also, a function generator (105) periodically change a center wavelength of the generated signals, and delivers signals to each a RF signal generator (106) and a signal processing unit (60) at the same time for optical propagation constant linearization by the change. From the above, a function generator (105) delivers signals to each a RF signal generator (106) and a signal processing unit (60) at the same time in order to obtain a tomography wherein a progress constant of a laser light is linearized.

Particularly, if the wavelength of light is changed (shifted) by a triangular-wave modulation signal and a sinusoidal (sine wave) modulation signal, interference signal space can be non-uniform and nonlinear. Therefore, a function generator (105) delivers the modulation signal to a signal processing unit (60) to perform the linearization by comparing the interference signal and the modulation signal. It is desirable that a reference parameter in the image processing process is 'linear change in the light progress constant according to time' than 'linear change in the wavelength according to time'. Particularly, since the light progress constant is equal to the reciprocal of the wavelength, a function generator (105) delivers a source signal driving a light source unit (100) to a signal processing unit (60).

Furthermore, a function generator (105) with a diagnostic unit (40) can deliver the generated signal to a space scanner (not shown) such as a galvanometer or a translation stage, in which one-dimensional depth information is converted to a two-dimensional cross section image or three-dimensional depth image. At this point, the space scanner can perform a repeated operation of converting one-dimensional depth information to a two-dimensional or three-dimensional image at integer multiples of the generated signal. That is, if a modulation signal generator (104) provides an optical amplifier (101) with the modulation signal, a function generator (105) can perform a linearization of the overall progress constant of light by providing a signal, basis of the modulation signal, to a diagnostic unit (40) and/or a signal processing unit (60).

A RF signal generator (106) generates a certain frequency RF signal. In the embodiments of the present invention, a RF signal generator (106) generates a RF signal within the MHz area with the generated signal from a function generator (105). For example, a RF signal generator (106) can repeatedly generate a RF signal within 597.18 MHz through 597.87 MHz with fixed frequency (100 kHz) generated from a function generator (105).

A DC voltage supply (107) provides a DC voltage of a fixed size to control an offset voltage. For example, a DC voltage supply (107) generates a DC voltage of a fixed size considering an offset voltage, and provides to a bias-tee.

A bias-tee (108) synthesizes a DC voltage from a DC voltage supply (107) and a RF signal from a RF signal generator (106), and provides a modulation signal to an optical amplifier (101). On this, a bias-tee (108) comprises a first input terminal for receiving a DC voltage, a second input terminal for receiving a RF signal and an output terminal for providing a modulation signal to an optical amplifier (101).

As mentioned above, a modulation signal generator (104) can be equipped with a separate light source unit (100), and can be placed in a light source unit (100).

Likewise, since a light having a changeable center wavelength from a light source unit (100), in which a center wavelength is changed by a modulation signal generator (104), it has no relationship to the length of a resonator. Thus, there can be wide variation of wavelength variable speed, and high-priced variable filter can be removed.

Figure 4:
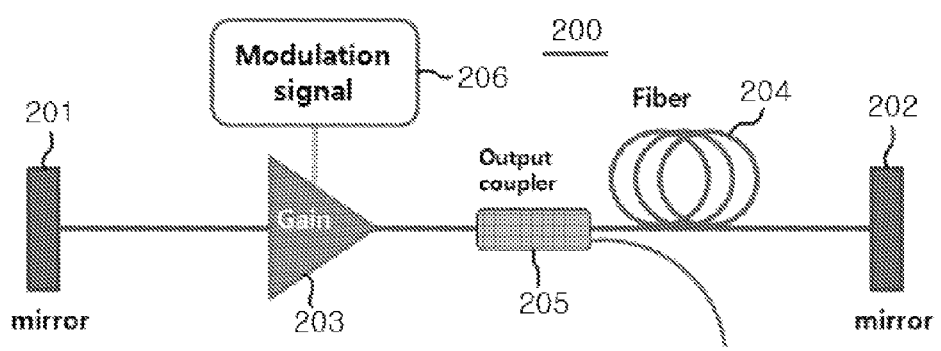
FIGS. 4 to 8 are block diagrams illustrating other embodiments of a light source unit shown in FIG. 1.

FIG. 4 is a block diagram illustrating other embodiments of a light source unit shown in FIG. 1.

Referring to FIG. 4, a light source unit (200) comprises an optical amplifier (203) providing optical gains to a linear resonator with mirrors (201, 202) at both ends; a dispersive compensation fiber (204) compensating the light dispersion of the resonator; and an output coupler (205) continuously waving light reflection and transmission in the resonator at certain rates.

A light source unit (200) shown in FIG. 4 and a light source unit (100) shown in FIG. 2 have different shapes resonators, other components of them are virtually identical, and they are the same in that an optical amplifier (203) directly receives the modulation signal from a modulation signal generator; and so a detailed description thereof will be omitted.

Figure 5:
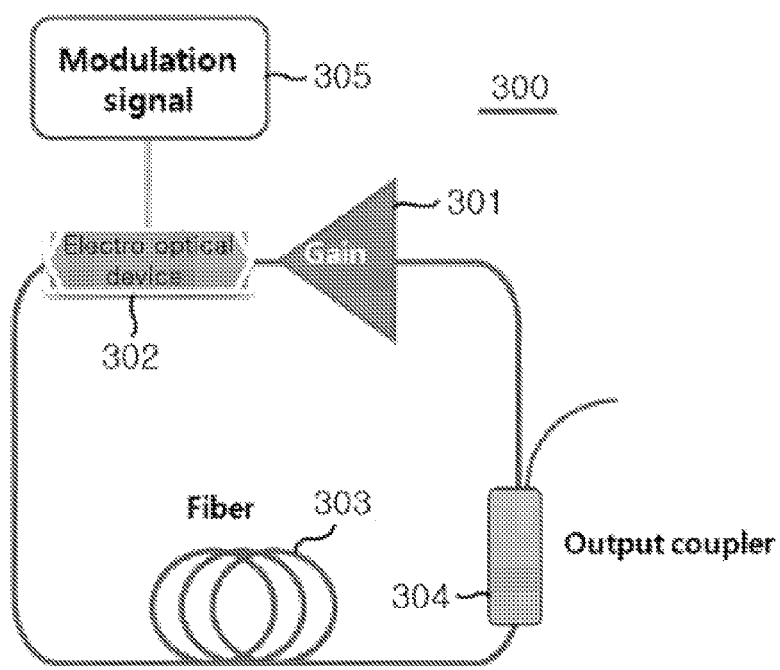

FIG. 5 is a block diagram illustrating other embodiments of a light source unit shown in FIG. 1.

Referring to FIG. 5, a light source unit (300) further comprises an electro optical device (302) in a linear shaped resonator for switching the progress of light depending on the intensity of light received from an optical amplifier (301). Meanwhile, a light source unit (300) and a light source unit (100) shown in FIG. 2 are virtually identical, except for an electro optical device.

Also, a light source unit (300) according to the embodiment of the present invention receives a modulation signal generated from a modulation signal generator (305).

Figure 6:
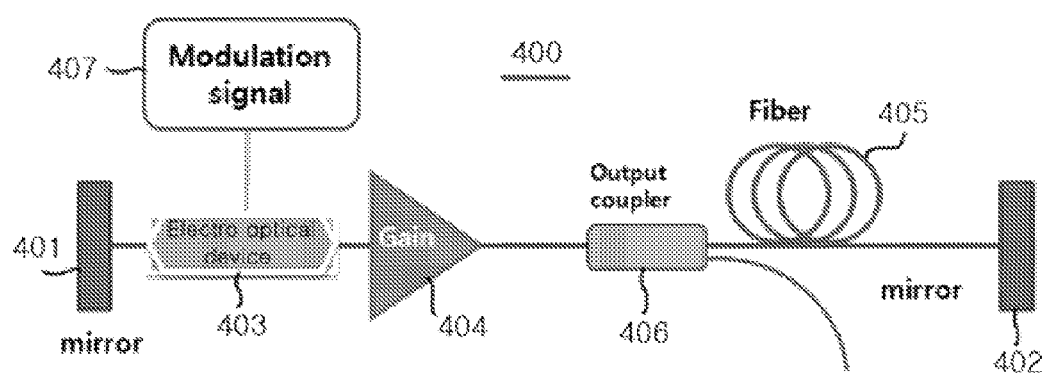

FIG. 6 is a block diagram illustrating other embodiments of a light source unit shown in FIG. 1.

Referring to FIG. 6, a light source unit (400) further comprises an optical amplifier (404) providing optical gains to a linear resonator with mirrors at both ends, and an electro optical device (403) switching the progress of light depending on the intensity of light received from an optical amplifier (404). At this point, an electro optical device (403) switching the light progress of a resonator, and it should not be limited by the terms of switching light received from an optical amplifier (404).

Also, a light source unit (400) according to the embodiment of the present invention, through an electro optical device (403), receives a modulation signal generated from a modulation signal generator (407).

Likewise, a light source unit (300, 400) shown in FIGS. 5 and 6 directly receives a modulation signal having a changeable center wavelength from a modulation signal generator (305, 407), through an electro optical device (302, 403).

A light source unit (300, 400), through an electro optical device (302, 403), directly receives a modulation signal having a changeable center wavelength from a modulation signal generator (305, 407), and there can be wide variation of wavelength variable speed, regardless of the length of a resonator. Also, production costs of a light source unit (300, 400) can be reduced by removing a high-priced variable filter.

Furthermore, if an electro optical device (302, 403) receives a modulation signal, compared to the case that an optical amplifier receives a modulation signal, it can be stably driven with a relatively lower power by repeating the rise and fall of optical intensity by switching passive optical waveguide, without switching positive optical gains.

Figure 7:
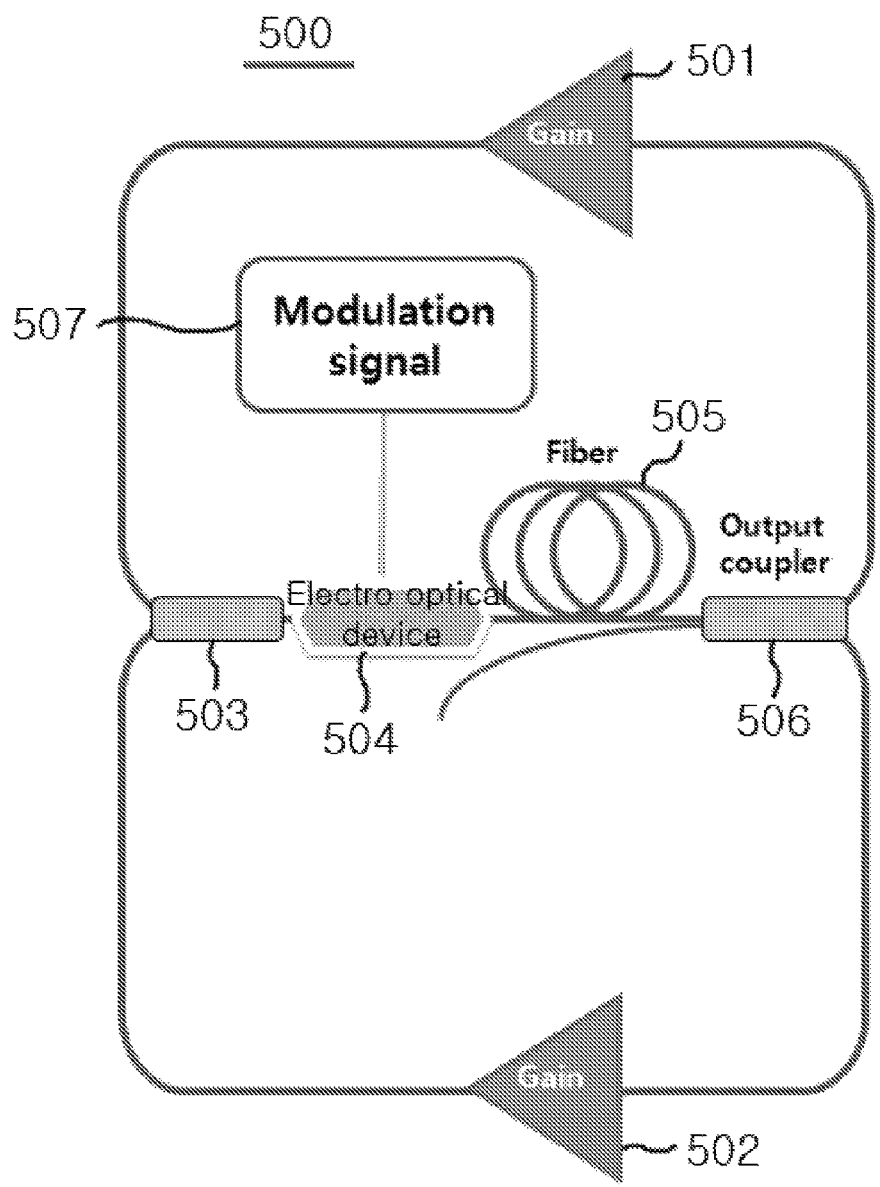
Figure 8:
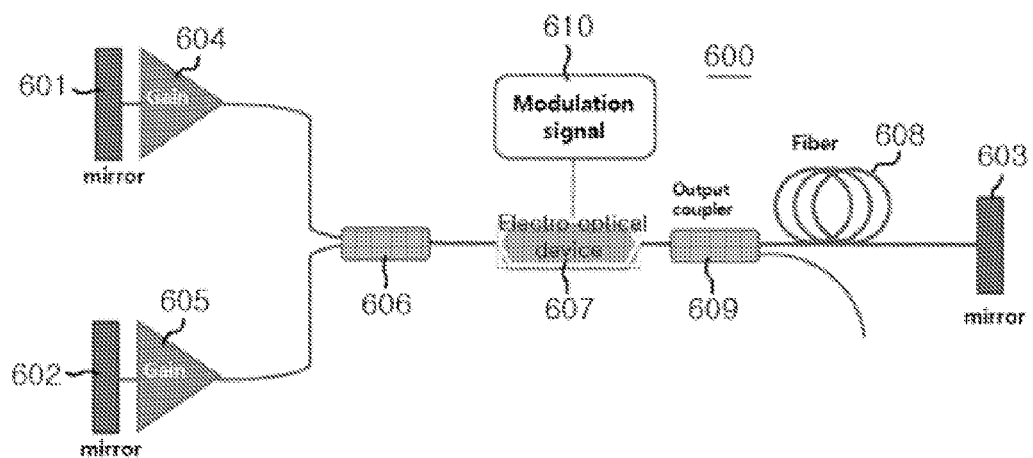

FIGS. 7 and 8 are block diagrams illustrating other embodiments of alight source unit shown in FIG. 1.

Referring to FIG. 7, a light source unit (500) comprises a plurality of optical amplifiers (501, 502) providing optical gains in ring shaped resonators, wherein a plurality of resonators are connected in parallel; a coupler (503) coupling lights each emitted by the plurality of optical amplifiers (501, 502); an electro optical device (504) witching the progress of light depending on the intensity of light coupled by the coupler (503), and receiving the modulation signal; a dispersive compensation fiber (505) for compensating the dispersion of light passed through an electro optical device (504); and an output coupler (506) continuously waving light reflection and transmission through a dispersive compensation fiber (505) at certain rates.

Referring to FIG. 8, a light source unit (600) comprises a plurality of optical amplifiers (604, 605) for providing optical gains each disposed in linear resonators, wherein a plurality of resonators are connected in parallel with mirrors (601, 602, 603) at both ends and a plurality of mirrors (601, 602) at one end; a coupler (606) for coupling lights each emitted by a plurality of optical amplifiers (604, 605); an electro optical device (607) for switching light progress depending on the light intensity connected by a coupler (606), and receiving the modulation signal; a dispersive compensation fiber (608) for compensating the optical dispersion through the resonator;

and an output coupler (609) for continuously waving light reflection and transmission of the resonator at certain rates.

Referring to FIGS. 7 and 8, optical amplifiers (501, 502, 604, 605) according to the embodiments of the present invention can provides different optical gains within a plurality of resonators connected in parallel.

A light source unit (500, 600) with parallel connected resonators can expand broadband and greatly improve output efficiency by disposing an electro optical device (504, 607) on a common optical path and an optical amplifier (501, 502, 604, 605) on a separate optical path.

Furthermore, it is efficiently controlled to input a modulation signal into an electro optical device (504, 607) disposed on a common optical path, compared to the case of inputting a modulation signal into each of optical amplifiers (501, 502, 604, 605) disposed on a plurality of resonators.

FIGS. 7 and 8 describe light source units (500, 600) with two parallel connected resonators of some different paths, but more resonators can be connected in parallel depending on broadband and output efficiency requested.

Figure 9:
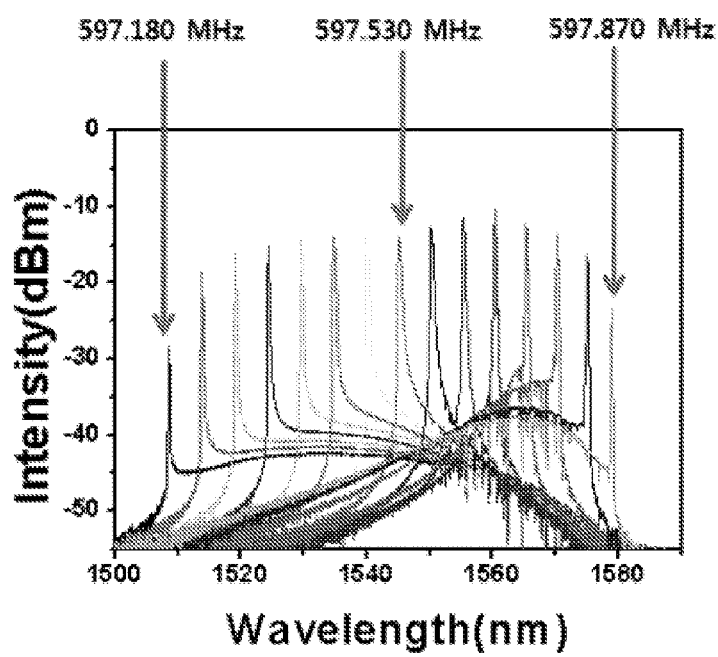
FIG. 9 is a graph showing the optical spectrum from a light source unit depending on frequency variation of a modulation signal.

FIG. 9 is a graph showing the optical spectrum from a light source unit depending on frequency variation of a modulation signal.

Referring to FIG. 9, a center wavelength of a modulation signal, output signal from a modulation signal generator, is changed, and in response generated wavelength from a light source unit is changed. Therefore, a center wavelength of light received from a light source unit is changed, if changing a frequency with a signal generator and a RF signal generator of a modulation signal generator outside of a resonator. Meanwhile, information about center wavelength changes of a modulation signal generator should be delivered to a signal processing unit of an imaging device at the same time to obtain a linear tomography by quantitatively linking the change of a center wavelength of light and the change of progress constant.

Likewise, an optical coherence tomography according to the embodiments of the present invention can efficiently replace a conventional variable filter by controlling a frequency of a modulation signal generator disposed outside a resonator, and changing a center wavelength of light from a light source unit. Furthermore, the present imaging device can expand broadband and greatly improve output efficiency by connecting a plurality of resonators in parallel and inputting a modulation signal into an electro optical device disposed on a common path of light.

Even though the above explained the preferred embodiments of the present invention, it will be understood that one having ordinary skill in the art can make various modifications and changes thereto within the scope of the present invention defined by the claims.

What is claimed is:

1. An optical coherence tomography using an active mode-locking fiber laser in order to obtain image information of a sample, comprising:
    a light source unit emitting light having a center wavelength which is periodically changed by a modulation signal received from outside of a resonator;
    a light separation unit separating light having a single path, which is emitted from the light source unit, into a first light and a second light having different paths;
    a reference unit disposed on a path through which the first light separated by the light separation unit progresses, and reflecting the first light;
    a diagnostic unit having the sample mounted thereon, disposed on a path of the second light separated by the light separation unit, and the second light is delayed more than the first light for a certain time to reflect the delayed light;
    a light coupling unit coupling the first light and the second light, which are progressed in different paths through the reference unit and the diagnostic unit, and in which mutual interference is generated therefrom; and
    a signal processing unit detecting and imaging data of the light received from the light coupling unit,
    wherein the light source unit, in which a plurality of resonators are connected in parallel, receives the modulation signal through the electro optical device disposed in the connection area of the resonators.

2. The optical coherence tomography as claimed in claim 1, wherein the light source unit comprising a plurality of optical amplifiers providing optical gains by each resonator of ring shaped resonators, wherein a plurality of resonators are connected in parallel; a coupler coupling lights each emitted by the plurality of optical amplifiers; an electro optical device switching the progress of light depending on the intensity of light coupled by the coupler, and receiving the modulation signal; a dispersive compensation fiber compensating the dispersion of light passed through the electro optical device; and an output coupler continuously waving light reflection and transmission of light passed through the dispersive compensation fiber at certain rates.

3. The optical coherence tomography as claimed in claim 1, wherein the light source unit comprising a plurality of optical amplifiers each disposed in linear resonators, wherein a plurality of resonators are connected in parallel with mirrors at both ends and a plurality of mirrors at one end, providing optical gains; a coupler coupling lights each emitted by a plurality of optical amplifiers; an electro optical device switching the progress of light depending on the intensity of light coupled by the coupler, and receiving the modulation signal; a dispersive compensation fiber compensating the optical dispersion in the resonator; and an output coupler continuously waving light reflection and transmission in the resonator at certain rates.

4. The optical coherence tomography as claimed in claim 2, further comprising a modulation signal generator for delivering a modulation signal having a changeable center frequency to the electro optical device, wherein the modulation signal generator comprises a function generator generating certain waveform signals, periodically changing the center frequency of the generated signals, delivering the signal to a signal processing unit to provide information about the linearization of a light progress constant; an RF signal generator generating the signal having a changeable center frequency into a certain range of RF signal; a DC voltage supply supplying a certain size DC voltage in order to control offset voltage; and a bias-tee providing the modulation signal to the optical amplifier by combining the DC voltage and the RF signal.

5. The optical coherence tomography as claimed in claim 2, wherein the optical amplifiers provide different optical gains in the plurality of resonators which are connected in parallel.

6. An optical coherence tomography comprising:
    a light source unit comprising an optical amplifier which is configured to provide optical gains to a resonator and to directly receive modulation signal generated from a modulation signal generator;
    a light separation unit configured to separate light having a single path, which is emitted from the light source unit, into a first light and a second light having different paths;

a reference unit disposed on a path through which the first light separated by the light separation unit progresses, and to reflect the first light;

a diagnostic unit, disposed on a path of the second light separated by the light separation unit, wherein the second light is delayed more than the first light for a predetermined time to reflect the delayed light;

a light coupling unit configured to couple the first light and the second light, which are progressed in different paths through the reference unit and the diagnostic unit, wherein mutual interference is generated therefrom; and a signal processing unit configured to process data of the light received from the light coupling unit, wherein the light source unit, in which a plurality of resonators are connected in parallel, is configured to receive the modulation signal through the electro optical device disposed in the connection area of the resonators.

7. The optical coherence tomography as claimed in claim 6, wherein the modulation signal generator is configured to deliver the modulation signal which has a changeable center wavelength to the optical amplifier, wherein the modulation signal generator comprises:

a function generator configured to generate waveform signals, periodically to change the center frequency of the generated signal, to deliver the modulation signal to a signal processing unit to perform the linearization of a light progress constant;

an RF signal generator configured to generate the signal having a changeable center frequency into a RF signal;

a DC voltage supply configured to supply a certain size DC voltage in order to control offset voltage; and a bias-tee configured to provide the modulation signal to the optical amplifier by combining the DC voltage and the RF signal.

* * * * *